United States Patent [19]

Gleckler et al.

[11] 4,035,267

[45] July 12, 1977

[54] DRY SHAMPOO USING CHITIN POWDER

[75] Inventors: George C. Gleckler; James C. Goebel, both of Stamford, Conn.

[73] Assignee: American Cyanamid Company, Stamford, Conn.

[21] Appl. No.: 718,725

[22] Filed: Aug. 30, 1976

[51] Int. Cl.² .................... C11D 7/46; C11D 7/32
[52] U.S. Cl. ............................. 252/548; 252/89 R; 252/544; 252/DIG. 13; 424/70
[58] Field of Search ................ 252/89 R, 162, 544, 252/548, 542, DIG. 13; 424/70

[56] References Cited

U.S. PATENT DOCUMENTS

| | | | |
|---|---|---|---|
| 1,208,069 | 12/1916 | Wittwer | 252/DIG. 13 X |
| 3,879,376 | 4/1975 | Vanlerberghe et al. | 252/89 X |
| 3,911,116 | 10/1975 | Balassa | 424/180 |

*Primary Examiner*—Harris A. Pitlick
*Attorney, Agent, or Firm*—Charles J. Fickey; John H. Engelmann

[57] ABSTRACT

A dry shampoo containing chitin powder is disclosed.

5 Claims, No Drawings

DRY SHAMPOO USING CHITIN POWDER

This invention relates to dry shampoos which are applied to the hair in powdered form, and then removed from the hair by brushing, thereby removing from the hair oil or sebum which becomes attached to the dry powder. More specifically, this invention relates to dry shampoos in which the active oil removing powder is chitin.

Dry powder shampoos are known, but have not been particularly popular largely because they are rather inefficient in removing sebum from the hair. Currently available dry powder shampoos consist of an active powder suspended in a carrier. When used, the powder is sprayed onto the hair, the carrier evaporates, the sebum from the hair is absorbed by the powder, and the powder is removed by brushing the hair. By this means, the hair is cleaned. Usually, these dry powder shampoos use starch as the active powder, and unfortunately starch tends to remain attached to the hair and is not readily removed after treatment. This is illustrated in Example II. While dry shampoos could be formulated with other powders such as activated carbon and alumina, such shampoos would not be desirable because the other powders are not biodegradable, and are difficult to remove from the hair. Alumina, for example, has been tested and found to be efficacious in removing sebum. However, it is unsuitable for use in a dry powder shampoo because it leaves behind a residue which causes the hair to feel gritty. Similarly, activated carbon leaves a residue on the hair which gives it a dark sooty appearance. Other powders such as pulverized clay, silica, and talc could be used in dry shampoo, but again these powders have the disadvantage that they are not biodegradable and tend to be difficult to remove from hair.

A truly efficacious dry powder shampoo would be useful in situations where the use of a water-base product is inconvenient or impossible. For example, bedridden patients might very well find it impossible to wash their hair with a water-based shampoo but could use a dry powder shampoo. In addition, people must wash and dry their hair in a hurry would welcome the convenience of a dry shampoo. Therefore, it would be desirable to have a dry powder shampoo and which was truly effective in removing oil from the hair, which did not at the same time present the hazards and the inconveniences of powders such as alumina, activated carbon, clay, silica and talc.

It is, therefore, an object of the present invention to provide an efficient, non-toxic biodegradable dry powder shampoo.

Accordingly, the present invention provides dry powder shampoo formulations based on chitin powder which is an ideal active ingredient for such use. Chitin itself, is a naturally occurring form of poly-N-acetyl glucosamine which may be isolated from several sources, expecially the exoskeleton of crustacea, such as shrimp. Chitin is readily broken down by enzymes found in body fluids, and thus, will present no hazard if it should accidently be swallowed, come in contact with an abraided area of the skin or get into the user's eyes. Chitin which does come into contact with body fluids, will be readily broken down into soluble, nontoxic materials. From the point of view of safety, therefore, chitin is desirable as an active ingredient in dry powder shampoos.

The size of the chitin particles making up the powder is not critical as long as it is appropriate for spraying. In other words, any particle which is suitable for spraying has the properties necessary for use in a spray shampoo. Generally, particles of about 10 to 75 microns in size are readily sprayable. For a discussion of characteristics of sprayable powders, see Cosmetics Science and Technology by Edward Sagarin, Interscience Publishers (1957) pp. 834–5, which is hereby incorporated by reference. It should be noted that chitin powder is ideal for spraying because the powder particles are well shaped, are insoluble in carrier fluids, and are not subject to agglomerative sedimentation.

Powdered chitin has a large surface area and is highly porous and therefore, readily takes up oily substances such as sebum, either by adsorption on the surface or by absorption into the pores. Hereinafter, the term absorption will be used to denote this take up of oily materials without regard to whether the actual process occurring is adsorption or absorption. In tests of the ability of dry powder shampoo compositions to remove synthetic sebum (prepared as shown in Example I) from hair tresses, chitin powder has been found to be much more active than starch powder. The tests were conducted by coating the hair with synthetic sebum and spraying the hair with the powder suspended in ethyl alcohol. The hair is then dried and brushed to remove the powder. The method and results are more fully described in Example II.

In formulating a dry powder shampoo, it is desirable that the active powder ingredients be suspended in a volatile liquid carrier to that this suspension may be sprayed onto the hair. This technique is desirable for two reasons. First, the presence of the volatile liquid allows the dry powder to penetrate closer to the scalp because it is carried there by the liquid, and second, the presence of the volatile liquid controls the undesirable tendency of the active powder to form a cloud of dust instead of remaining on the user's hair. In addition, certain volatile fluids act to dissolve the sebum from the hair and carry it into the active powder prior to the evaporation of the volatile liquid. The quantity of the carrier should be sufficient to accomplish its objectives but not so great as to excessively wet the hair. The ratio of carrier to chitin powder may vary from about 5 to 1 to 1:1 by weight.

Many organic substances or mixtures thereof, may serve as the volatile liquid. The primary considerations in the selection of such a liquid are the relative toxicity of the vapor and the irritancy of the liquid to the user's skin. Other important considerations in selecting a volatile liquid are the flammability of such liquid and the exact degree of volatility. While obviously, the invention is operative even if a highly flammable substance is used as the volatile liquid, it is preferable either to avoid the use of highly flammable liquids, or to use them in conjunction with non-flammable liquids.

Liquids with boiling points ranging from about −30° to about 82° C. may be used as the volatile liquid in conjunction with the chitin powder. Compounds with suitable properties include esters such as ethyl acetate and methyl acetate; ketones such as methyl ethyl ketone and acetone; hydrocarbons, such as the straight chained alkanes, butanes, pentane and hexane; cyclic hydrocarbons such as cyclopropane, cyclobutane, cyclopentane, and cyclohexane; branched chain hydrocarbons such as 2,2-dimethyl propane, the methyl pentanes, the dimethyl pentanes and the dimethyl butanes;

alcohols, such as ethyl alcohol and iso-propyl alcohol, ethers, such as dimethyl ether, diethyl ether, diisopropyl ether, the methyl ethers of ethyl, isopropyl, propyl, n-butyl, t-butyl and isobutyl alcohols, and the ethyl ethers of n-propyl, isopropyl, isobutyl, t-butyl and 2-butyl alcohols; and fluorine containing alkyl halides, such as dichloro-difluoromethane, 1-chloro, 1,1-difluoroethane, octofluorocyclobutane, 1,2-dichloro-1,1,2,2-tetrofluoromethane, dichloro-fluoromethane and fluoro-trichloromethane.

As noted above, the volatile liquid may consist of either a single pure material or a combination of materials. It is preferred that liquids at either extreme of the boiling point range not be used above, but rather as part of a mixture of substances acting as a carrier. For example, extremely volatile liquids, such as dichloro difluoromethane may be mixed with a relatively non-volatile liquid such as ethanol. As noted above, in selecting a carrier substance, consideration should be given to the fire hazard which the substance might present. Thus, the ethers and hydrocarbons are rather hazardous materials, while the alkyl fluorides present no fire hazard. It is preferred that the volatile liquid contain a non-flammable fluorocarbon or mixture thereof if the highly flammable hydrocarbons or ethers are used.

The dry powder shampoo may be applied either from aerosol cans, or from a hand operated spray device. If the dry powder shampoo is sprayed from an aerosol can, a propellant substance must be used. The choice of propellant material is not critical and any nontoxic substance which develops the requisite pressure may be used to perform the essentially mechanical function of driving the volatile liquid and the powder out of the aerosol container. All propellants which are commonly used in aerosol cans are, of course, suitable for use in this application. Low boiling substances suitable for use as the volatile liquid may also serve as a propellant.

The following examples are provided for illustrative purposes only and may include particular features of the invention. However, the examples should not be construed as limiting the invention. Many variations of which are possible without departing from the spirit or scope thereof.

EXAMPLE I

Preparation of Synthetic Sebum

The following ingredients were mixed and warmed to approximately 30° C. to form a clear solution.

| | |
|---|---|
| Squalene | 5 parts |
| Olive Oil | 32 |
| Paraffin Oil, Saybolt Visc 335/350 | 20 |
| Oleic Acid | 14 |
| Linoleic Acid | 6 |
| Lauric Acid | 1 |
| Myristic Acid | 2 |
| Palmitic Acid | 4 |
| Stearic Acid, USP | 2 |
| Spermwax | 6 |
| Coconut Oil | 4 |
| Mixed Sterols | 4 |
| | 100 |

Upon cooling to room temperature, a slight haze develops.

This formula is a modification of one given by G. Barnett and D. H. Powers in the *Toilet Goods Association* December, 1955, p. 24.

EXAMPLE II

The Effectiveness of Various Dry Powder Shampoos

To one end of a 3 g. hair tress was applied approximately 0.24 g. (8% of the hair weight) artificial sebum prepared according to Example I. The tress was given 175 brush strokes to distribute the sebum evenly, and then weighed to determine the weight of sebum actually deposited. A mixture of 2 grams of ethyl alcohol and 0.5 g. of the powder to be tested were sprayed onto the free hanging tress. The alcohol was allowed to evaporate, and the tress was again weighed to determine the weight of powder deposited. The tress was then given 60 brush strokes to remove the powder, and dried in a vacuum oven at 70° C. overnight. A final weighing was then made to determine the amount of sebum removed by the powder. A sample of synthetic sebum lost only about 2% of the weight under the overnight drying conditions. Two separate runs were done with chitin powder, and four were done with starch. The results for each powder were averaged and are shown in the table below.

TABLE

| | Sebum Removal by Various Powders | | | |
|---|---|---|---|---|
| Wt. of hair at 0% RH | % Sebum[1] | Powder | Wt. Powder applied g. | % Sebum removed |
| 3.068 | 8.2 | Chitin[2] | 0.19 | 38 |
| 3.090 | 8.1 | Starch[3] | 0.19 | −15[5] |
| 3.132 | 8.0 | None[4] | 0.011[6] | 0.5 |

[1]Synthetic sebum prepared as shown in Example I
[2]−325 mesh
[3]−325 mesh
[4]2.5 grams of alcohol containing no powder were sprayed on the hair. Subsequently this sample was treated in the normal manner.
[5]The negative number indicates that the sample of hair gained weight in the test. This gain in weight results from starch adhering to the hair.
[6]Weight gained by tress after 2.5 g alcohol sprayed on and allowed to evaporate.

We claim:
1. A method of cleaning hair which comprises: spraying onto said hair a sprayable powder chitin being suspended in a non-toxic volatile liquid carrier having a boiling point between about −30° and 82° C., allowing said liquid carrier to evaporate, and removing the residual powder from the hair.
2. The method of claim 1 wherein the carrier is a low molecular weight volatile alcohol.
3. The method of claim 1 wherein the carrier is ethanol.
4. The method of claim 1 wherein the carrier comprises about 1 to 5 parts by weight per part of chitin.
5. The method of claim 1 wherein the carrier is a low molecular weight hydrocarbon.

* * * * *